US010891790B2

(12) United States Patent
Walle-Jensen et al.

(10) Patent No.: US 10,891,790 B2
(45) Date of Patent: Jan. 12, 2021

(54) METHODS AND SYSTEMS FOR ALIGNMENT OF A SUBJECT FOR MEDICAL IMAGING

(71) Applicant: Stryker European Operations Limited, Carrigtwohill (IE)

(72) Inventors: Jorgen Walle-Jensen, Vancouver (CA); Lina Gurevich, Vancouver (CA); Gregory Vincent Browne, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 1023 days.

(21) Appl. No.: 15/337,986

(22) Filed: Oct. 28, 2016

(65) Prior Publication Data

US 2017/0124768 A1 May 4, 2017

Related U.S. Application Data

(60) Provisional application No. 62/248,199, filed on Oct. 29, 2015.

(51) Int. Cl.

*G06T 19/00* (2011.01)
*A61K 49/00* (2006.01)
(Continued)

(52) U.S. Cl.

CPC .......... *G06T 19/006* (2013.01); *A61B 5/0071* (2013.01); *A61K 49/0034* (2013.01);
(Continued)

(58) Field of Classification Search

CPC .............. A61B 5/0071; A61K 49/0034; G06T 19/006; G06T 2207/10016;
(Continued)

(56) References Cited

U.S. PATENT DOCUMENTS

2004/0206913 A1* 10/2004 Costa .................. A61B 5/0059 250/458.1
2005/0272971 A1 12/2005 Ohnishi et al.
(Continued)

FOREIGN PATENT DOCUMENTS

EP 1761160 B1 12/2012

OTHER PUBLICATIONS

Canadian Office Action dated Mar. 5, 2019 for CA Application No. 3,002,873 filed on Apr. 23, 2018, five pages.
(Continued)

*Primary Examiner* — Michael T Rozanski
(74) *Attorney, Agent, or Firm* — Morrison & Foerster LLP

(57) ABSTRACT

Methods and systems for alignment of a subject for medical imaging are disclosed, and involve providing a reference image of an anatomical region of the subject, the anatomical region comprising a target tissue, processing the reference image to generate an alignment reference image, displaying the alignment reference image concurrently with real-time video of the anatomical region, and aligning the real-time video with the alignment reference image to overlay the real-time video with the alignment reference image. Following such alignment, the subject may be imaged using, for example, fluorescence imaging, wherein the fluorescence imaging may be performed by an image acquisition assembly aligned in accordance with the alignment.

80 Claims, 7 Drawing Sheets

(51) Int. Cl.
*G06T 7/33* (2017.01)
*A61B 5/00* (2006.01)

(52) U.S. Cl.
CPC ...... *G06T 7/33* (2017.01); *G06T 2207/10016* (2013.01); *G06T 2207/10064* (2013.01); *G06T 2207/30048* (2013.01); *G06T 2207/30104* (2013.01); *G06T 2207/30196* (2013.01); *G06T 2207/30204* (2013.01); *G06T 2210/41* (2013.01)

(58) Field of Classification Search
CPC . G06T 2207/10064; G06T 2207/30048; G06T 2207/30104; G06T 2207/30196; G06T 2207/30204; G06T 2210/41; G06T 7/33
See application file for complete search history.

(56) References Cited

U.S. PATENT DOCUMENTS

| | | | | |
|---|---|---|---|---|
| 2010/0312122 | A1* | 12/2010 | Yazdanfar .......... | A61K 49/0021 600/476 |
| 2014/0203491 | A1 | 7/2014 | Kern | |
| 2014/0303491 | A1 | 10/2014 | Shekhar et al. | |
| 2015/0223668 | A1* | 8/2015 | Gilboa ............... | A61B 1/00128 600/103 |

OTHER PUBLICATIONS

European Search Report dated May 7, 2019, for EP Patent Application No. 16858543.8, filed Oct. 28, 2016, six pages.

International Preliminary Report on Patentability dated May 11, 2018 for International Application No. PCT/CA2016/051254, filed on Oct. 28, 2016, seven pages.

International Search Report and Written Opinion dated Jan. 23, 2017 for International Application No. PCT/CA2016/051254, filed on Oct. 28, 2016, ten pages.

Notice of Allowance dated Apr. 1, 2020, directed to CA Application No. 3,002,873; 1 page.

* cited by examiner

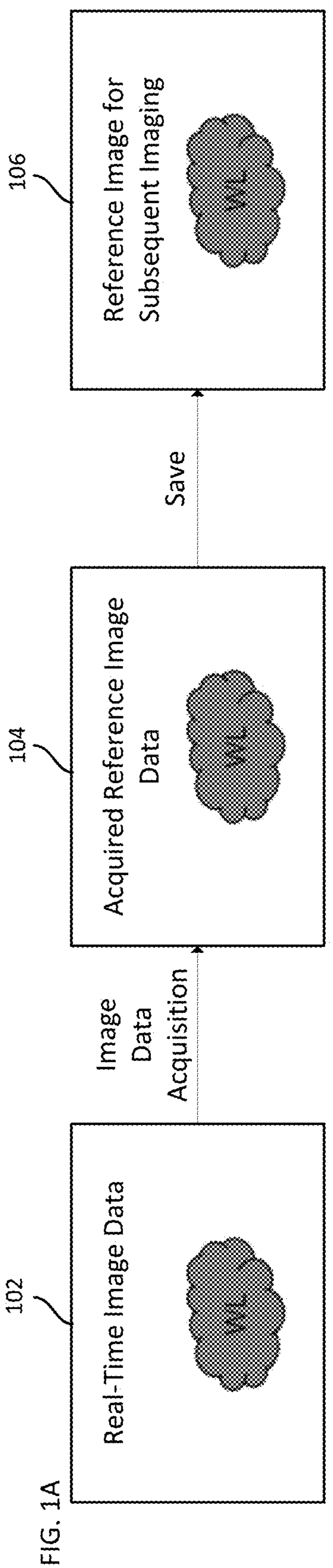

FIG. 1A
102
Real-Time Image Data
WL
Image Data Acquisition
104
Acquired Reference Image Data
WL
Save
106
Reference Image for Subsequent Imaging
WL

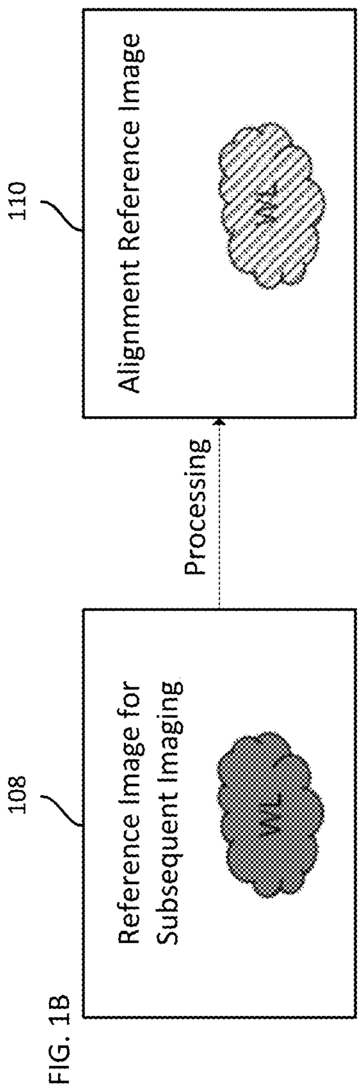

FIG. 1B
108
Reference Image for Subsequent Imaging
WL
Processing
110
Alignment Reference Image
WL

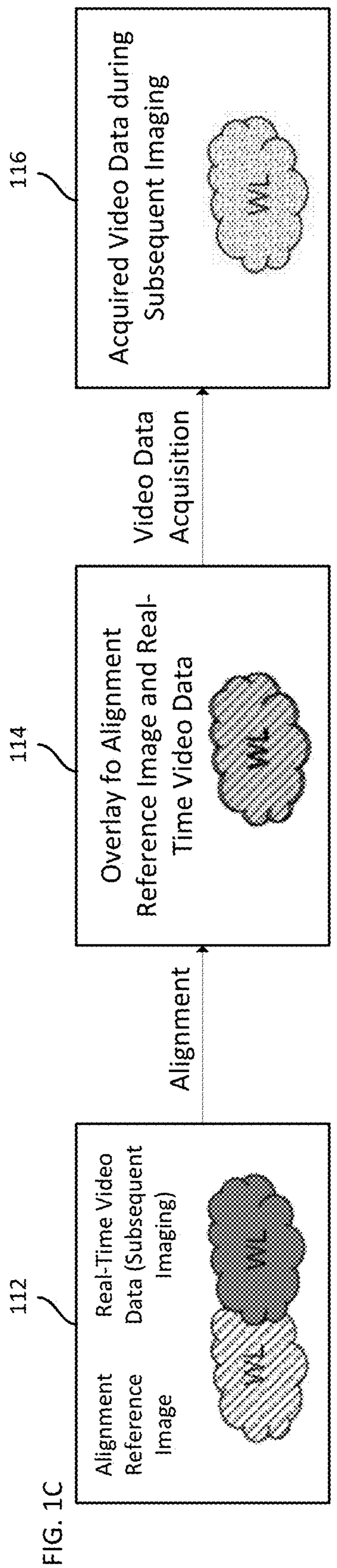

FIG. 1C
112
Alignment Reference Image
Real-Time Video Data (Subsequent Imaging)
WL
WL
Alignment
114
Overlay fo Alignment Reference Image and Real-Time Video Data
WL
Video Data Acquisition
116
Acquired Video Data during Subsequent Imaging
WL

METHODS AND SYSTEMS FOR ALIGNMENT OF A SUBJECT FOR MEDICAL IMAGING

REFERENCE TO RELATED APPLICATIONS

This application claims priority to U.S. Provisional Application Ser. No. 62/248,199 filed Oct. 29, 2015, titled "METHODS AND SYSTEMS FOR ALIGNMENT OF A SUBJECT FOR MEDICAL IMAGING," which is hereby incorporated by reference in its entirety.

FIELD OF THE INVENTION

This disclosure relates generally to medical imaging, and more particularly to facilitating alignment of a subject for medical imaging.

BACKGROUND OF THE INVENTION

Medical imaging relates to techniques and processes of producing a visual representation of an aspect of a subject's body for clinical analysis and/or medical intervention. Examples of medical imaging include computed tomography, ultrasound, and magnetic resonance imaging (MRI). Medical imaging can also include optical modalities such as fluorescence medical imaging.

In medical imaging applications, careful setup of the subject for imaging is important. Specifically, in instances where image data is going to be compared with previous or future images, it is desirable to reproduce the positioning of the imaging means (e.g., the camera or imaging head) in relation to the anatomical region of interest of the subject, or vice versa, such that the field of view and orientation of the region of interest is the same or close to the same relative to the imaging means for all images. Alignment of the positioning in this fashion helps to ensure reproducibility over time and minimizes inaccuracies in the assessment of subjects undergoing assessments. Furthermore, such alignment techniques facilitate the use of quantitative image analysis to aid in the comparative assessments.

Currently available technologies for alignment of a subject to be imaged are cumbersome. Typically, positioning of the subject and/or the imaging means is based on approximation of the positioning of the subject by the operator by visual comparison of the subject to a previously acquired image. Such an approach may be time consuming; may be difficult to perform when the subject has issues with mobility; and may be affected by the level of operator experience, visual subjective judgment, and the amount of time the operator takes to perform the setup. Alignments achieved using such an approach may be inaccurate or unreliable. Accordingly, less than optimal imaging may result.

SUMMARY OF THE INVENTION

In accordance with some embodiments, there is provided a method for alignment of a subject for medical imaging. The method includes providing a reference image of an anatomical region of the subject, the anatomical region including a target tissue, processing the reference image to generate an alignment reference image, displaying the alignment reference image concurrently with real-time video of the anatomical region, and aligning the real-time video with the alignment reference image to overlay the real-time video with the alignment reference image. The method further includes acquiring the real-time video and processing the real-time video to quantify the target tissue. The quantification of the target tissue includes calculating a dimension of the target tissue, which may be applicable to, for example, wound care or to a surgical intervention. In an embodiment, the reference image comprises a white light image. In an embodiment, processing the reference image to generate the alignment reference image comprises applying transparency to the reference image.

In accordance with some embodiments, there is provided an alignment system for alignment of a subject for medical imaging. The alignment system includes a camera assembly for image data acquisition, a display having a user interface, a processor configured to communicate with the user interface, a non-transitory computer-readable storage medium having instructions stored thereon to be executed by the processor. The instructions cause the processor to perform operations including providing a reference image of the anatomical region of the subject, the anatomical region including a target tissue, processing the reference image to generate an alignment reference image, displaying on the user interface the alignment reference image concurrently or simultaneously with real-time video of the anatomical region, and aligning the real-time video with the alignment reference image to overlay the real-time video with the alignment reference image. The alignment system may be used to aid the quantitative image analysis in comparative assessments over time.

In some embodiments, a method of aligning an image acquisition assembly is provided, the method comprising: receiving a reference image of an anatomical region of a subject, the anatomical region comprising a target tissue; processing the reference image to generate an alignment reference image; displaying the alignment reference image on a display concurrently with real-time video of the anatomical region acquired from the image acquisition assembly; dynamically updating the displayed real-time video to reflect adjustments to a current alignment of the image acquisition assembly relative to the anatomical region of the subject; and displaying the real-time video and the alignment reference image as overlaid with one another when the current alignment of the image acquisition assembly is aligned with a predefined alignment associated with the reference image.

In some embodiments, the method comprises: illuminating, by a light source included in the system, the target tissue to induce fluorescence emission; when the current alignment of the image acquisition assembly is aligned with a predefined alignment associated with the reference image, capturing, by the image acquisition assembly, a time series of fluorescence input data from the fluorescence emission, the fluorescence input data capturing transit of the fluorescence agent through the tissue, wherein the image acquisition assembly is configured to receive fluorescence images for fluorescence medical imaging.

In some embodiments of the method, the fluorescence medical imaging comprises quantitative fluorescence imaging, qualitative fluorescence imaging, or a combination thereof.

In some embodiments of the method, the illuminating and the capturing are initiated in response to determining that the current alignment is aligned with the predefined alignment.

In some embodiments, the method comprises: in response to detecting that the current alignment is not aligned with the predefined alignment, ceasing the illuminating and the capturing.

In some embodiments of the method, inducing fluorescence emission comprises inducing fluorescence emission from an endogenous fluorophore, from an exogenous fluorescence imaging agent, or a combination thereof.

In some embodiments of the method, the exogenous fluorescence imaging agent comprises indocyanine green (ICG).

In some embodiments, the method comprises: quantifying the fluorescence input data.

In some embodiments, the method comprises: while the current alignment is aligned with the predefined alignment, acquiring the real-time video and processing the real-time video to quantify the target tissue.

In some embodiments of the method, the acquiring and processing of the real time video is initiated in response to detecting that the current alignment is aligned with the predefined alignment.

In some embodiments of the method, quantifying the target tissue comprises calculating a dimension of the target tissue.

In some embodiments, the method comprises: in response to detecting that the current alignment is not aligned with the predefined alignment, ceasing the acquiring and processing of the real-time video.

In some embodiments of the method, acquiring the reference image comprises acquiring the reference image from a camera.

In some embodiments of the method, acquiring the reference image comprises retrieving stored data representing the reference image.

In some embodiments of the method, the reference image is a white light image, a white light-derived image, a fluorescence image, a fluorescence-derived image, or a combination of any one or more thereof.

In some embodiments of the method, processing the reference image to generate the alignment reference image comprises applying transparency to the reference image.

In some embodiments, the method comprises: displaying an alignment indicator on the display, wherein the alignment indicator indicates a difference between the current alignment and the predefined alignment, and wherein the alignment indicator is distinct from the real-time video and the alignment reference image.

In some embodiments of the method, indicating a difference between the current alignment and the predefined alignment comprises displaying a line between a first portion of the alignment reference image depicting a portion of the anatomical region and a corresponding portion of the real-time video depicting the portion of the anatomical region.

In some embodiments of the method, the line indicates a direction in which the current alignment should be adjusted to align with the predefined alignment.

In some embodiments, the method comprises: in response to detecting that the current alignment is aligned with the predefined alignment, displaying on the display a notification that the current alignment is aligned with the predefined alignment, wherein the notification is distinct from the real-time video and the alignment reference image.

In some embodiments, the method comprises: in response to detecting that the current alignment is aligned with the predefined alignment, providing one of an auditory and a haptic notification that the current alignment is aligned with the predefined alignment.

In some embodiments of the method, the reference image comprises one or both of a white light image and a processed image.

In some embodiments of the method, the real-time video comprises one or both of a white light image and a processed image.

In some embodiments, the method comprises: applying an algorithm to determine that the current alignment is aligned with the predefined alignment.

In some embodiments of the method, applying the algorithm comprises calculating an image transformation matrix including a translation and a rotation for aligning the current alignment and the predefined alignment.

In some embodiments, an alignment system is provided, the alignment system comprising: a display; an image acquisition assembly; a processor; and memory storing instructions that, when executed by the processor, cause the processor to: receive a reference image of an anatomical region of a subject, the anatomical region comprising a target tissue; process the reference image to generate an alignment reference image; display the alignment reference image on a display concurrently with real-time video of the anatomical region acquired from the image acquisition assembly; update the displayed real-time video to reflect adjustments to a current alignment of the image acquisition assembly relative to the anatomical region of the subject; and display the real-time video and the alignment reference image as overlaid with one another when the current alignment of the image acquisition assembly is aligned with a predefined alignment associated with the reference image.

In some embodiments of the system, the instructions cause the processor to: illuminate, by a light source included in the system, the target tissue to induce fluorescence emission; when the current alignment of the image acquisition assembly is aligned with a predefined alignment associated with the reference image, capture, by the image acquisition assembly, a time series of fluorescence input data from the fluorescence emission, the fluorescence input data capturing transit of the fluorescence agent through the tissue, wherein the image acquisition assembly is configured to receive fluorescence images for fluorescence medical imaging.

In some embodiments of the system, the fluorescence medical imaging comprises quantitative fluorescence imaging, qualitative fluorescence imaging, or a combination thereof.

In some embodiments of the system, the illuminating and the capturing are initiated in response to determining that the current alignment is aligned with the predefined alignment.

In some embodiments of the system, the instructions cause the processor to, in response to detecting that the current alignment is not aligned with the predefined alignment, cease the illuminating and the capturing.

In some embodiments of the system, inducing fluorescence emission comprises inducing fluorescence emission from an endogenous fluorophore, from an exogenous fluorescence imaging agent, or a combination thereof.

In some embodiments of the system, the exogenous fluorescence imaging agent comprises indocyanine green (ICG).

In some embodiments of the system, the instructions cause the processor to quantify the fluorescence input data.

In some embodiments of the system, the instructions cause the processor to, while the current alignment is aligned with the predefined alignment, acquire the real-time video and process the real-time video to quantify the target tissue.

In some embodiments of the system, the acquiring and processing of the real time video is initiated in response to detecting that the current alignment is aligned with the predefined alignment.

In some embodiments of the system, quantifying the target tissue comprises calculating a dimension of the target tissue.

In some embodiments of the system, wherein the instructions cause the processor to, in response to detecting that the current alignment is not aligned with the predefined alignment, cease the acquiring and processing of the real-time video.

In some embodiments of the system, acquiring the reference image comprises acquiring the reference image from a camera.

In some embodiments of the system, acquiring the reference image comprises retrieving stored data representing the reference image.

In some embodiments of the system, the reference image is a white light image, a white light-derived image, a fluorescence image, a fluorescence-derived image, or a combination of any one or more thereof.

In some embodiments of the system, processing the reference image to generate the alignment reference image comprises applying transparency to the reference image.

In some embodiments of the system, the instructions cause the processor to display an alignment indicator on the display, wherein the alignment indicator indicates a difference between the current alignment and the predefined alignment, and wherein the alignment indicator is distinct from the real-time video and the alignment reference image.

In some embodiments of the system, indicating a difference between the current alignment and the predefined alignment comprises displaying a line between a first portion of the alignment reference image depicting a portion of the anatomical region and a corresponding portion of the real-time video depicting the portion of the anatomical region.

In some embodiments of the system, the line indicates a direction in which the current alignment should be adjusted to align with the predefined alignment.

In some embodiments of the system, the instructions cause the processor to, in response to detecting that the current alignment is aligned with the predefined alignment, display on the display a notification that the current alignment is aligned with the predefined alignment, wherein the notification is distinct from the real-time video and the alignment reference image.

In some embodiments of the system, the instructions cause the processor to, in response to detecting that the current alignment is aligned with the predefined alignment, provide one of an auditory and a haptic notification that the current alignment is aligned with the predefined alignment.

In some embodiments of the system, the reference image comprises one or both of a white light image and a processed image.

In some embodiments of the system, the real-time video comprises one or both of a white light image and a processed image.

In some embodiments of the system, the instructions cause the processor to apply an algorithm to determine that the current alignment is aligned with the predefined alignment.

In some embodiments of the system, applying the algorithm comprises calculating an image transformation matrix including a translation and a rotation for aligning the current alignment and the predefined alignment.

In some embodiments, a non-transitory computer readable storage medium is provided, the non-transitory computer readable storage medium storing instructions, wherein the instructions are executable by a system having a display, an image acquisition assembly, and a processor to cause the system to: receive a reference image of an anatomical region of a subject, the anatomical region comprising a target tissue; process the reference image to generate an alignment reference image; display the alignment reference image on a display concurrently with real-time video of the anatomical region acquired from the image acquisition assembly; update the displayed real-time video to reflect adjustments to a current alignment of the image acquisition assembly relative to the anatomical region of the subject; and display the real-time video and the alignment reference image as overlaid with one another when the current alignment of the image acquisition assembly is aligned with a predefined alignment associated with the reference image.

In some embodiments of the non-transitory computer readable storage medium, the instructions cause the processor to: illuminate, by a light source included in the system, the target tissue to induce fluorescence emission; when the current alignment of the image acquisition assembly is aligned with a predefined alignment associated with the reference image, capture, by the image acquisition assembly, a time series of fluorescence input data from the fluorescence emission, the fluorescence input data capturing transit of the fluorescence agent through the tissue, wherein the image acquisition assembly is configured to receive fluorescence images for fluorescence medical imaging.

In some embodiments of the non-transitory computer readable storage medium, the fluorescence medical imaging comprises quantitative fluorescence imaging, qualitative fluorescence imaging, or a combination thereof.

In some embodiments of the non-transitory computer readable storage medium, the illuminating and the capturing are initiated in response to determining that the current alignment is aligned with the predefined alignment.

In some embodiments of the non-transitory computer readable storage medium, the instructions cause the processor to, in response to detecting that the current alignment is not aligned with the predefined alignment, cease the illuminating and the capturing.

In some embodiments of the non-transitory computer readable storage medium, inducing fluorescence emission comprises inducing fluorescence emission from an endogenous fluorophore, from an exogenous fluorescence imaging agent, or a combination thereof.

In some embodiments of the non-transitory computer readable storage medium, the exogenous fluorescence imaging agent comprises indocyanine green (ICG).

In some embodiments of the non-transitory computer readable storage medium, the instructions cause the processor to quantify the fluorescence input data.

In some embodiments of the non-transitory computer readable storage medium, the instructions cause the processor to, while the current alignment is aligned with the predefined alignment, acquire the real-time video and process the real-time video to quantify the target tissue.

In some embodiments of the non-transitory computer readable storage medium, the acquiring and processing of the real time video is initiated in response to detecting that the current alignment is aligned with the predefined alignment.

In some embodiments of the non-transitory computer readable storage medium, quantifying the target tissue comprises calculating a dimension of the target tissue.

In some embodiments of the non-transitory computer readable storage medium, wherein the instructions cause the processor to, in response to detecting that the current alignment is not aligned with the predefined alignment, cease the acquiring and processing of the real-time video.

In some embodiments of the non-transitory computer readable storage medium, acquiring the reference image comprises acquiring the reference image from a camera.

In some embodiments of the non-transitory computer readable storage medium, acquiring the reference image comprises retrieving stored data representing the reference image.

In some embodiments of the non-transitory computer readable storage medium, the reference image is a white light image, a white light-derived image, a fluorescence image, a fluorescence-derived image, or a combination of any one or more thereof.

In some embodiments of the non-transitory computer readable storage medium, processing the reference image to generate the alignment reference image comprises applying transparency to the reference image.

In some embodiments of the non-transitory computer readable storage medium, the instructions cause the processor to display an alignment indicator on the display, wherein the alignment indicator indicates a difference between the current alignment and the predefined alignment, and wherein the alignment indicator is distinct from the real-time video and the alignment reference image.

In some embodiments of the non-transitory computer readable storage medium, indicating a difference between the current alignment and the predefined alignment comprises displaying a line between a first portion of the alignment reference image depicting a portion of the anatomical region and a corresponding portion of the real-time video depicting the portion of the anatomical region.

In some embodiments of the non-transitory computer readable storage medium, the line indicates a direction in which the current alignment should be adjusted to align with the predefined alignment.

In some embodiments of the non-transitory computer readable storage medium, the instructions cause the processor to, in response to detecting that the current alignment is aligned with the predefined alignment, display on the display a notification that the current alignment is aligned with the predefined alignment, wherein the notification is distinct from the real-time video and the alignment reference image.

In some embodiments of the non-transitory computer readable storage medium, the instructions cause the processor to, in response to detecting that the current alignment is aligned with the predefined alignment, provide one of an auditory and a haptic notification that the current alignment is aligned with the predefined alignment.

In some embodiments of the non-transitory computer readable storage medium, the reference image comprises one or both of a white light image and a processed image.

In some embodiments of the non-transitory computer readable storage medium, the real-time video comprises one or both of a white light image and a processed image.

In some embodiments of the non-transitory computer readable storage medium, the instructions cause the processor to apply an algorithm to determine that the current alignment is aligned with the predefined alignment.

In some embodiments of the non-transitory computer readable storage medium, applying the algorithm comprises calculating an image transformation matrix including a translation and a rotation for aligning the current alignment and the predefined alignment.

In some embodiments, a kit for aligning an image acquisition assembly is provided, the kit comprising any of the systems described herein and a fluorescence imaging agent.

In some embodiments, a fluorescence imaging agent is provided, the fluorescence imaging agent for use in any of the methods or in any of the systems described herein for aligning an image acquisition assembly.

In some embodiments of the fluorescence imaging agent, aligning the image acquisition assembly comprising aligning during for blood flow imaging, tissue perfusion imaging, lymphatic imaging, or a combination thereof.

In some embodiments of the fluorescence imaging agent, blood flow imaging, tissue perfusion imaging, and/or lymphatic imaging comprises blood flow imaging, tissue perfusion imaging, and/or lymphatic imaging during an invasive surgical procedure, a minimally invasive surgical procedure, or during a non-invasive surgical procedure.

In some embodiments of the fluorescence imaging agent, the invasive surgical procedure comprises a cardiac-related surgical procedure or a reconstructive surgical procedure.

In some embodiments of the fluorescence imaging agent, the cardiac-related surgical procedure comprises a cardiac coronary artery bypass graft (CABG) procedure.

In some embodiments of the fluorescence imaging agent, wherein the CABG procedure is on pump or off pump.

In some embodiments, any of the methods, systems, computer-readable storage media, kits, imaging agents, or other embodiments described herein may be used for aligning an image acquisition assembly for lymphatic imaging.

In some embodiments, any of the methods, systems, computer-readable storage media, kits, imaging agents, or other embodiments described herein may be used for aligning an image acquisition assembly for blood flow imaging, tissue perfusion imaging, or a combination thereof.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE DRAWINGS

FIGS. 1A to 1C illustrate a schematic example of a method according to some embodiments;

DETAILED DESCRIPTION OF THE INVENTION

Figure 2:
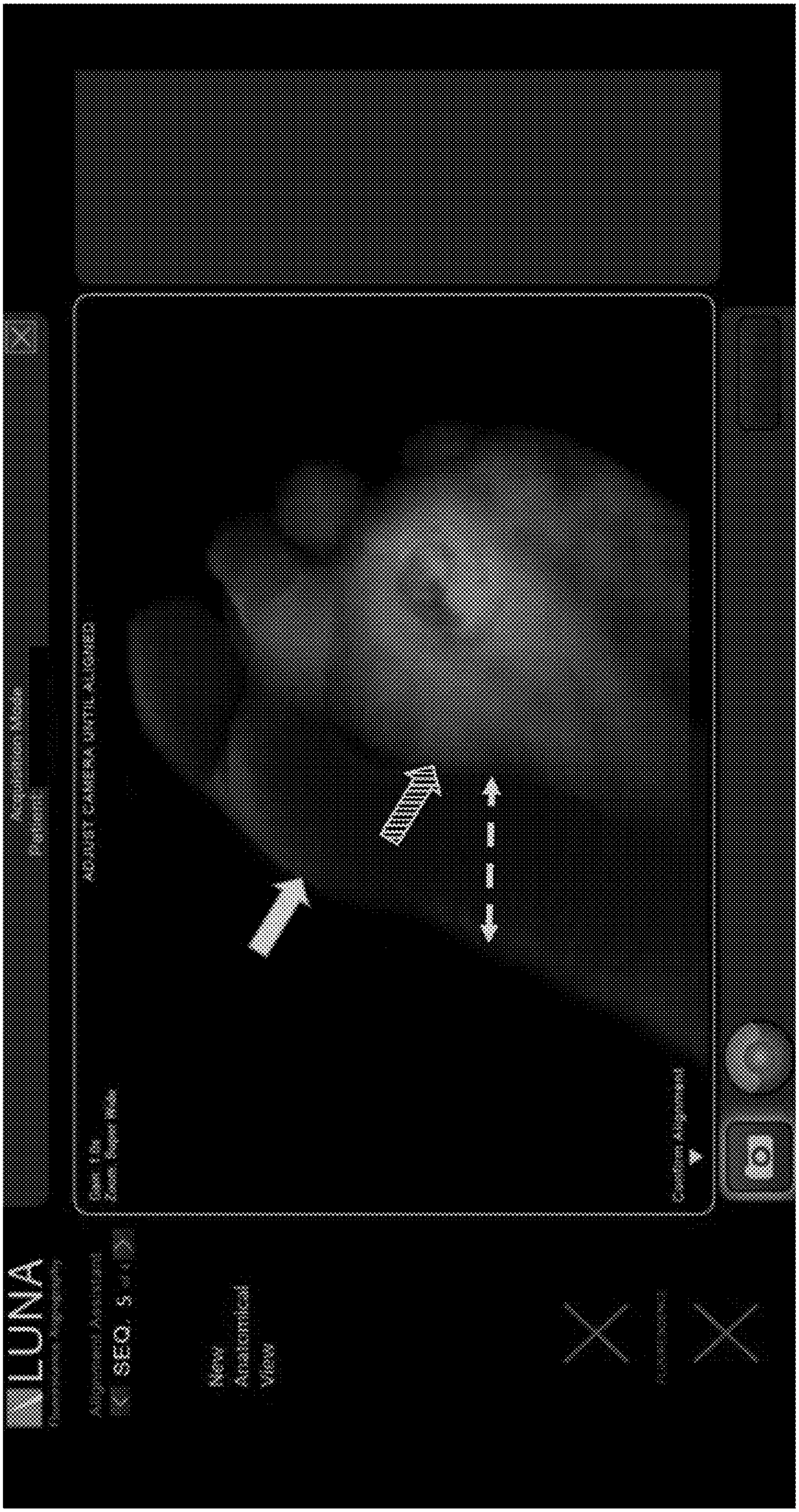
FIG. 2 illustrates an exemplary clinical application of the method according to some embodiments.

Reference will now be made in detail to implementations and embodiments of various systems, methods, and techniques, examples of which are illustrated in the accompanying drawings. Various methods of aligning an image, alignment systems, and non-transitory computer readable storage media storing instructions are described herein. Although at least two variations of the methods of aligning an image, alignment systems, non-transitory computer readable storage media, kits are described, other variations may include aspects of the systems, methods, and non-transitory computer readable storage media described herein combined in any suitable manner having combinations of all or some of the aspects described.

The time between acquisition of image data for a subject can be variable (e.g., hours, days, or months). In order to compare image data acquired over time, areas being imaged may need to be aligned prior to initiating image acquisition. For example, the distance, angle, and rotation of the imaging means relative to the area being imaged should, in some embodiments, be substantially the same for all the image data acquired. According to the various aspects, the methods and systems for optical imaging use a reference image from previously acquired image data as a "ghosted" (e.g., semi-transparent, translucent, or outlined) overlay, over live (real-time video) image data to assist the imaging device operator with achieving reproducible alignment of the anatomical site of the subject.

In accordance with some embodiments, there is provided a method for alignment of a subject for medical imaging using optical modalities, such as, for example, fluorescence imaging.

In accordance with some embodiments, a method of aligning an image acquisition assembly is provided, the method comprising: receiving a reference image of an anatomical region of a subject, the anatomical region comprising a target tissue; processing the reference image to generate an alignment reference image; displaying the alignment reference image on a display concurrently with real-time video of the anatomical region acquired from the image acquisition assembly; dynamically updating the displayed real-time video to reflect adjustments to a current alignment of the image acquisition assembly relative to the anatomical region of the subject; and displaying the real-time video and the alignment reference image as overlaid with one another when the current alignment of the image acquisition assembly is aligned with a predefined alignment associated with the reference image.

The methods and systems for aligning the subject according to the various embodiments may aid in qualitative and/or quantitative image analysis such as, for example, qualitative and/or quantitative image analysis in wound care. In this regard, for example, a change in the wound over time, such as a change in wound dimensions (e.g., diameter, area), or a change in tissue perfusion in the wound and/or around the peri-wound, may be more reproducibly, reliably, and/or accurately tracked over time with the application of the methods and systems for aligning the subject.

The methods and systems for aligning the subject according to the various embodiments may also aid in qualitative and/or quantitative image analysis of other clinical imaging applications, such as qualitative and/or quantitative image analysis of surgical interventions and/or assessments. The methods and systems for alignment may be used, for example, to aid in alignment of successive images intra-operatively in one surgical intervention or assessment, or to aid in alignment of images in multiple surgical interventions or assessments, such as an initial intervention and/or assessment and one or more follow up interventions and/or assessments. For example, multiple intra-operative images may be recorded and qualitatively and/or quantitatively compared or collectively analyzed, with the aid of the methods and systems for alignment, during cardiac-related surgery (e.g., cardiac coronary artery bypass graft (CABG) surgery on and/or off pump), cardiovascular surgery, gastrointestinal surgery, plastic/reconstructive surgery (e.g., flap procedures), lymphatic imaging surgery, or any surgery or any forms of invasive surgical procedures where comparison and/or analysis of multiple intra-operative images at various time points may be useful. In this regard, for example, a change in the target tissue over time (either on a short time scale, intra-operatively, or a longer scale, between successive surgical interventions or assessments) such as a change in perfusion in the tissue and/or around the target tissue (e.g., in the peri-wound), may be more reproducibly, reliably, and accurately tracked over time with the application of the methods and systems for aligning the subject.

As is schematically illustrated in FIGS. 1A to 1C, in various embodiments, the reference image of the anatomical region of the subject comprising the target tissue to be imaged may be derived from acquired reference image data of the anatomical region (e.g., reference image data sequence, real-time image data). As shown in FIG. 1A, at element 102, real-time image data may be acquired. For example, a camera or other image capture device may acquire real-time image data of the anatomical region. As shown by element 104, reference image data may be acquired in accordance with the real-time image data, such as by capturing and/or acquiring a reference image by a camera, image sensor, or other image-capture device. In some embodiments, reference image data may be received or retrieved from computer storage or from a third party, rather than or in addition to being captured or acquired in accordance with real-time image data. In some embodiments, the reference image may be, for example, a single frame selected from the reference image data. In various other embodiments, the reference image may be derived from a plurality of frames. For example, the reference image may be a composite or a mosaic of a plurality of reference image frames, or a reference image sequence. In various embodiments, the reference image data (e.g., the reference image) may be acquired and/or generated (e.g., when the reference image data is processed raw data) during an initial assessment of the subject, or during an assessment chosen as a reference assessment for subsequent imaging. As shown at element 106, the reference image may be saved or stored for retrieval at a later time, such as during future imaging sessions. As shown at elements 108 and 110, the reference image (e.g., the saved or stored reference image) further processed to generate the alignment reference image (FIG. 1B). The resulting alignment reference image or a portion thereof may define the alignment to be used on subsequent image data acquisitions, and may be user-selectable. The processing of the reference image to generate the alignment reference image may, for example, comprise applying various levels of transparency to the reference image to generate a semi-transparent or translucent alignment reference image, it may comprise processing the reference image to generate an image comprising highlighted outlines or contours, it may comprise other image processing to generate an alignment reference image suitable to be viewed by a user who is simultaneously viewing subsequent-image data, or a combination thereof. In some embodiments, the alignment reference image may be an outline or contour of the reference image. In some embodiments, the alignment reference image may be a portion of the reference image. In some embodiments, the alignment reference image may be a shape generated by 3D sensors. In various embodiments, the alignment reference image may be further processed to incorporate or remove color or any other features as to make it more visually distinct compared to the video image data, for example by increasing or decreasing saturation, by falsely colorizing, by removing color and converting an the alignment reference image to grayscale or black and white, by brightening or darkening, or by increasing or decreasing the prominence of one or more colors in the alignment reference image.

In various embodiments, the reference image may be previously stored and retrievable for use in the methods and systems discussed herein. In other embodiments, the methods and systems may further involve acquiring the reference image data for providing the reference image and the alignment reference image.

A skilled person will appreciate that although the methods herein are described in the context of processing a reference image to generate an alignment reference image by, for example, applying a level of transparency to the reference image, a real-time video or a portion thereof may be processed in a similar manner instead of processing a reference image. Thus in some embodiments, a level of transparency or other image processing techniques may be applied to a real-time video as opposed to a reference image.

In some embodiments, the alignment reference image or a portion thereof may be displayed to the user as a static or fixed image concurrently or simultaneously with live (real-time video) data of the anatomical region of the subject comprising the target tissue to be imaged during subsequent imaging. This technique is schematically illustrated in element 112 of FIG. 1C, and is further illustrated in the clinical example in FIG. 2, where the solid white arrow indicates the alignment reference image of the subject's foot, and the pattern arrow indicates video of image data misaligned (with the dotted double arrow indicating the misalignment) with the alignment reference image. The alignment reference image may be displayed to the user, for example, as a background image or as an overlay, or as a partially transparent or translucent image. With both the alignment reference image and live video data displayed, the user may align the video data until it generally overlays the alignment reference image, as shown schematically in element 114 of FIG. 1C. As shown in element 116, when alignment is achieved, the user may begin acquisition of the imaging data (e.g., fluorescence imaging data) as is described in more detail in the Examples section. Acquisition as contemplated by element 116 may include, in some embodiments, capturing and/or storing image data beyond merely transiently capturing the image data for the purpose of displaying real-time video data for alignment. In some embodiments, acquisition as contemplated in element 116 may include capturing white light images and/or fluorescence images, in addition to any other image types contemplated herein. According to some embodiments, image data acquisition may be triggered to begin automatically once a quantified and/or desired level of alignment is achieved. For example, a system may verify that sufficient alignment has been achieved by measuring a linear misalignment and determining whether the linear misalignment is below a predefined threshold distance, or by dynamically calculating a similarity score by comparing the live data and the alignment reference image, and determining whether the similarity score is above a predefined threshold. When sufficient alignment is achieved, the system may alert the user (e.g., by displaying an indication) and may automatically begin image data acquisition. In some embodiments, when sufficient alignment is achieved, then it may be said that a current alignment corresponding to live video is "aligned" with a predefined alignment corresponding to the alignment reference image. If sufficient alignment is not achieved between the current alignment and the predefined alignment, then it may be said that the current alignment and predefined alignment are not "aligned." In some embodiments, sufficient alignment may be determined in accordance with any of the techniques discussed above in this paragraph, it may require that optimal alignment according to a sensitivity of a system is achieved (e.g., "exact" alignment according to precision of instrumentation), and/or it may require that alignment is achieved within a predefined threshold or percentage (e.g., approximate alignment).

While FIGS. 1A to 1C schematically illustrate "WL" (e.g., white light) images, a person of ordinary skill in the art would appreciate that the techniques described with reference to FIGS. 1A to 1C and elsewhere herein may be equally applicable to other kinds of images and other kinds of imaging, such as fluorescence imaging. For example, in some embodiments, the real-time image data, reference image, alignment reference image, and real-time video data may comprise white light images, while the acquired video or image data during subsequent imaging may comprise fluorescence images. Other combinations or arrangements of white light images, fluorescence images, other image types, and combinations thereof may also be used.

As a result of the alignment, according to various embodiments, the image data acquired during subsequent imaging generally corresponds in, for example, distance, angle rotation, and/or other parameters a user may select to the initial reference image data, thus facilitating relevant comparison over time that generally corresponds to the same anatomical location over time. In some embodiments where different cameras are used to acquire the reference image and the real-time video, the selected parameters of the cameras may be matched as closely as possible. For example, a field of view of the cameras may be substantially the same. In some embodiments, there may be some differences with respect to resolution of the cameras, or with respect to other properties or parameters of the cameras. A skilled person will appreciate that the more differences there are between the parameters of the cameras, the less alignment accuracy may be achieved with respect to the methods discussed herein. The level of alignment accuracy required can vary depending on the clinical application.

In various embodiments, an alignment indicator may be provided to the user with regard to an acceptable range of overlap between the alignment reference image and the video image data during the alignment. For example, a boundary or a marker such as a bounding rectangle or cursor with or without a quantified representation of the degree of alignment may be generated and displayed to the user relating to one of or both the alignment reference image or a portion thereof and the video image data within which the video image data must be aligned with the alignment reference image. An example of a boundary rectangle is shown by the white rectangle with rounded corners in FIG. 2. In some embodiments, when an acceptable overlap of bounding rectangles is detected, the application can automatically change the color of the ghosted reference image to indicate to the user that the live video is now sufficiently aligned with the reference image (e.g., within an acceptable degree of alignment), and to signal to the user that further adjustment is not necessary. For example, the ghosted reference image may be shown in red when the live video is misaligned with the reference image, and after a suitable alignment range is achieved, the reference image may turn green. In some embodiments, improved accuracy in automatic alignment detection may be achieved by utilizing medical tattoos. In some such embodiments, rather than relying on bounding rectangles, the software can narrow the matching search to the specific shape of the tattoo. Once both shapes overlap within a pre-defined tolerance threshold (e.g., alignment range), feedback (e.g., visual, sound, tactile) can be generated for the user to indicate that the alignment has been achieved and that further adjustment is not necessary. In some embodiments, the image acquisition system may be configured to automatically begin image data acquisition once both shapes (e.g., rectangles, medical tattoos, etc.) overlap within the pre-defined tolerance threshold. Such an alignment threshold-based automated image data acquisition feature may be useful, for example, when the clinical application requires very close image alignment or when the application makes a stable camera position difficult to maintain. In various embodiments, an auto-matching algorithm may be used as an aid for achieving the alignment, wherein the auto-matching algorithm may calculate an alignment score indicative of the alignment from 0% to 100%, with 100% representing the best attainable alignment, or may calculate another quantitative metric of alignment. The alignment score may be based, for example, on a calculation of the percentage of area of an identified shape or bounding rectangle of a region in the real-time video, which is overlapping the area of a corresponding matched shape or bounding rectangle in the reference image. An acceptable alignment area overlap range may include, for example, an alignment overlap range within about 100% to about 99%, about 99% to about 97%, about 97% to about 95%, about 95% to about 93%, or about 93% to about 90%. As another example, an auto-matching algorithm may comprise an image registration algorithm that compares image features and calculates an optimal best fit alignment of the real-time video and the reference image, and that calculates a corresponding image transformation matrix including translations and rotations that would be required to correctly align the real-time video to the reference image or vice-versa. Thresholds may be set for maximum acceptable values of translation or rotation values as calculated by the image registration algorithm, so that the images may be identified as sufficiently aligned or not sufficiently aligned according to the calculated values. Additionally or alternatively, feedback may be provided to the user to indicate the magnitude and/or direction of mis-alignment between the real-time image and the reference image, according to the magnitude and/or direction of the translations and/or rotations as predicted to be required by the image registration algorithm, such that a user may execute the required and indicated rotations and/or translations based on the provided feedback. In some embodiments, a system having an automatically-controlled physical component may implement the required translations or rotations, as determined by an auto-matching algorithm, in response to the required translations or rotations being detected. A skilled person will appreciate that the particular implementation detail in regard to the acceptable alignment overlap range, or the thresholds for calculated translation and rotation values, may vary from application to application. For example, in the context of an invasive surgical procedure such as cardiac bypass surgery, a greater alignment may be desirable, for example, to compare images before, during and after the procedure than, for example, in the context of less invasive imaging (e.g., wound care).

Various types of image data (e.g., reference image data, video image data, or a combination thereof) may be acquired, aligned, viewed, and/or generated in accordance with the various embodiments. Examples of the image data with reference to fluorescence imaging include:

a color or gray scale white light (WL) image of the anatomy of the subject comprising the target tissue to be imaged; or a fluorescence image of the target tissue; or processed image data mapped to a false color or range of colors, such processing and color mapping being used to identify or emphasize a range of fluorescence intensity; or processed image data mapped to a false color or range of colors, such processing and color mapping being used to identify or emphasize changes in fluorescence characteristics over time; or desaturated image data; or a combination of any one or more of the above.

The image data may be either colorized, grayscale, or desaturated and may comprise one or more regions of interest. In the context of this specification, a "color image" of the anatomy of the subject refers to a white-light image or image sequence or video of the anatomy of the subject.

In accordance with some embodiments, there is provided an alignment system configured for alignment of a subject for medical imaging. In some embodiments, an alignment system is provided, the alignment system comprising: a display; an image acquisition assembly; a processor; and memory storing instructions that, when executed by the processor, cause the processor to: receive a reference image of an anatomical region of a subject, the anatomical region comprising a target tissue; process the reference image to generate an alignment reference image; display the alignment reference image on a display concurrently with real-time video of the anatomical region acquired from the image acquisition assembly; update the displayed real-time video to reflect adjustments to a current alignment of the image acquisition assembly relative to the anatomical region of the subject; and display the real-time video and the alignment reference image as overlaid with one another when the current alignment of the image acquisition assembly is aligned with a predefined alignment associated with the reference image.

Figure 3:
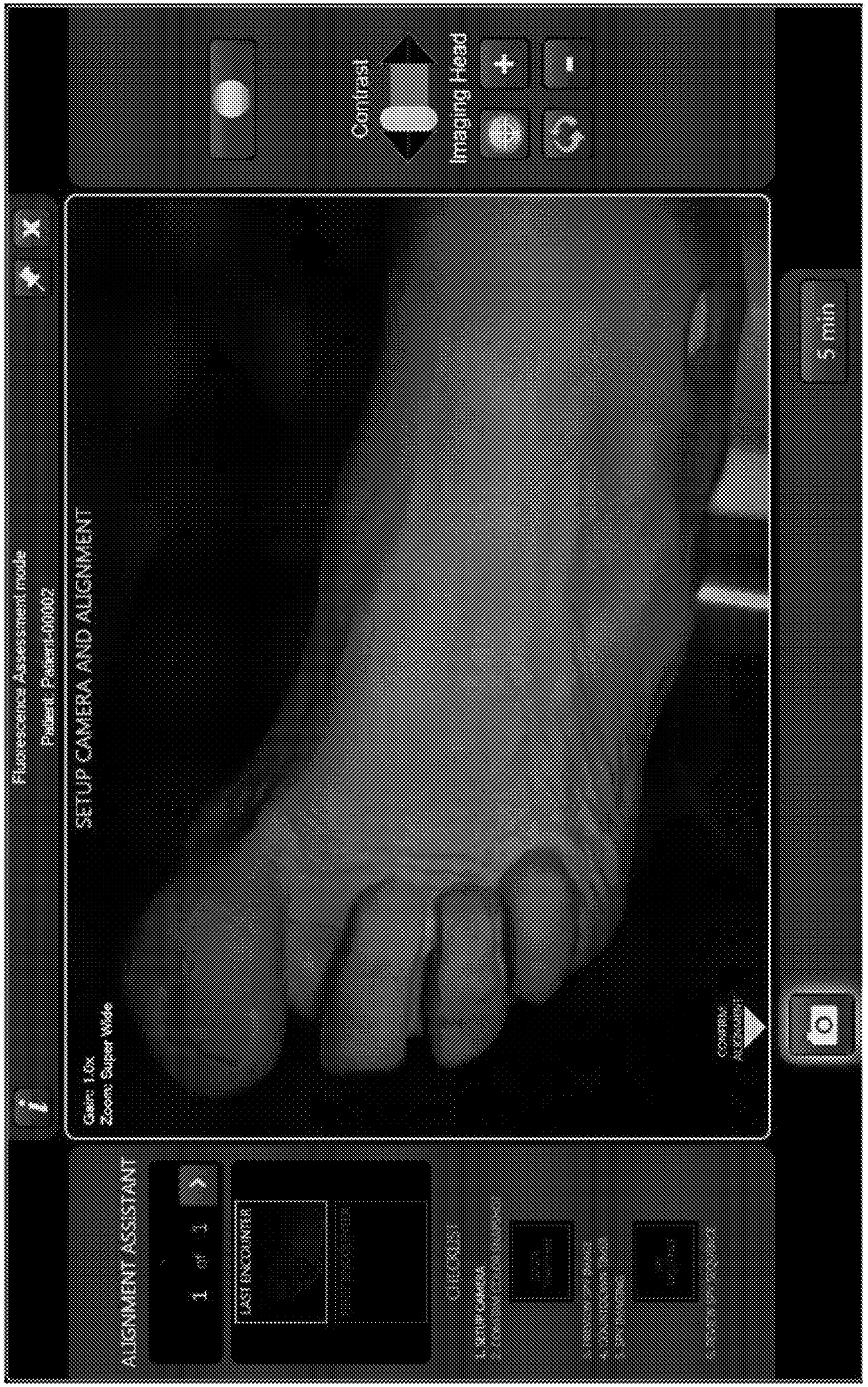
FIG. 3 illustrates an example alignment reference image according to some embodiments.
Figure 4C:
FIGS. 4A to 4E illustrate example alignment of real-time video data with an alignment reference image according to some embodiments.
Figure 4B:
Figure 4E:
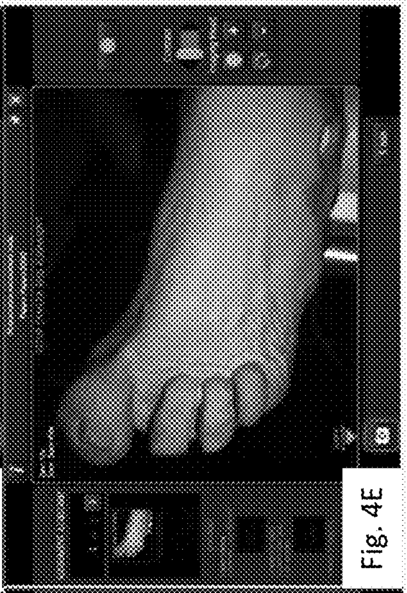
Figure 4A:
Figure 4D:

FIG. 3 illustrates an example of the user interface displayed on the display of the alignment system for alignment of a subject for medical imaging according to an embodiment. The camera assembly of the alignment system (not shown) may be moved by a user into position and held stationary. In some embodiments, the camera assembly may have a camera arm (a multi-directional arm) for providing stability for image alignment, acquisition, or a combination thereof. In some embodiments, a camera arm may be used that features one or more motorized or otherwise controllable degrees of freedom of motion of the camera, and automated motion of the camera within these controllable degrees of freedom may be performed to assist with optimizing the image alignment. A skilled person will appreciate that although the camera arm may be helpful in assisting to keep the camera assembly in a stationary position, it is not necessary. In various embodiments, the camera assembly can be held by hand or supported by some other means. In various embodiments, the camera assembly can be a camera of a medical imaging system (e.g., a fluorescence medical imaging system) as is discussed in the exemplary embodiments below, or it can be another camera assembly imaging in the same optical imaging plane as the camera of the medical imaging system. In some embodiments, the camera assembly may be configured to provide 3D imaging.

As is illustrated in FIG. 3, an image may be acquired for alignment purposes (i.e., a reference image, an alignment reference image or both). In the example in FIG. 3, the reference image is acquired with NIR illumination (NIR camera assembly), but in various embodiments it can be taken in any other way that allows for video with substantially similar imaging conditions.

A processor of the alignment system may be configured to execute instructions stored on local or remote transitory or non-transitory computer readable storage medium, and to cause the system to execute any one or more of the steps described in connection with methods or techniques herein. In some embodiments, the processor may be configured to process the reference image to generate an alignment reference image as was described above. The software may facilitate transforming the reference image into a semi-transparent image (i.e., the alignment reference image), or transforming the image in any one or more of the manners discussed above. The reference image, the alignment reference image, or both may be stored in any suitable storage medium, such as local or remote computer memory, hard disk space, RAM, and/or any transitory or non-transitory computer-readable storage medium, for use in subsequent imaging and/or assessments.

In subsequent imaging (i.e., the next time the patient is being imaged, or during an imaging session thereafter) and/or assessments, the alignment reference image may be retrieved from storage and used for alignment of the video image data. FIGS. 4A to 4E illustrate progressive alignment of video image data (indicated by the pattern arrow) with the alignment reference image (indicated by the solid white arrow) using an alignment system in accordance with the description herein, where the alignment in FIGS. 4A to 4E progressively improves until adequate or sufficient alignment is achieved in FIG. 4E.

Once alignment is achieved (e.g., FIG. 4E), the user can initiate acquisition of the desired image data sequence using the medical imaging system, or the system can automatically initiate acquisition upon detecting that sufficient alignment has been achieved. According to some embodiments, another alignment reference image may be acquired during such medical imaging for alignment during further imaging. Alternatively, the alignment reference image from the first assessment may be used for all subsequent imaging. Thus, for example, in various embodiments, the user may choose to align to an alignment reference image from the most recent image data sequence acquired, or to the first alignment reference image from the first image data sequence acquired. The selection of the alignment reference image (e.g., first image or later acquired image) may depend on clinical circumstances. For example, in some embodiments, using the first-acquired alignment reference image may be better from a pure alignment perspective, while the last-acquired alignment reference image might be better from a practical standpoint as the anatomy of the subject might change over time, for example, due to surgery (e.g., amputation, implantation or grafting), wound changes, swelling, other conditions, or a combination of such factors. Multiple alignment reference images may be acquired and stored, in accordance with one or more of the techniques discussed herein, corresponding to multiple assessment views of the target tissue, as appropriate or desired, for example to image different views of the target tissue from different angles or from different working distances.

In accordance with some embodiments, the alignment system may be a stand-alone imaging system or a component of a medical imaging system. For example, in fluorescence medical imaging, the alignment system may be used with a fluorescence imaging system, or it may be a component of the fluorescence imaging system. In an embodiment, the fluorescence imaging system comprises: a light source configured to illuminate a tissue of a subject to induce fluorescence emission from a fluorescence imaging agent in the tissue; an image acquisition assembly configured to acquire a time series of fluorescence input data from the fluorescence emission, the fluorescence input data capturing transit of the fluorescence agent through the tissue, and a processor assembly configured to process the time series of fluorescence input data. In some embodiments, the fluorescence medical imaging system (or other medical imaging systems) may be considered to be a part of any of the systems described herein.

Further aspects of such an example fluorescence imaging system are described in more detail in the Examples section.

In yet further aspects, there may be provided a kit including an alignment system, a medical imaging system (e.g., a fluorescence medical imaging system) and an imaging agent (e.g., a fluorescence imaging agent, for example, a fluorescence dye such as ICG or methylene blue). In yet further aspects, there is provided a kit including, a medical imaging system (e.g., a fluorescence medical imaging system) comprising an alignment system and an imaging agent wherein the medical imaging system is configured to perform the method for alignment of a subject for medical imaging. In some embodiments, the alignment system and/or medical imaging system included in the kit may be any of the alignment systems described herein, and/or any system configured to perform any of the methods performed herein.

One skilled in the art will appreciate that, although the various exemplary embodiments are illustrated in the Examples section in the context of fluorescence image data, the systems and methods may be applied to other medical imaging applications comprising the use of optical imaging modalities.

EXAMPLES

A Fluorescence Medical Imaging System for Acquisition of Image Data

In some embodiments, a system for alignment of a subject for medical imaging may be used with or as a component of a medical imaging system such as, for example, a fluorescence medical imaging system for acquiring fluorescence medical image data. An example of such a fluorescence medical imaging system is the fluorescence imaging system 20 schematically illustrated in FIG. 5. In this embodiment, the fluorescence imaging system 20 is configured to acquire a time series of fluorescence signal intensity data (e.g., images, video) capturing the transit of a fluorescence imaging agent through the tissue.

The fluorescence imaging system 20 (FIG. 5) comprises a light source 22 to illuminate the tissue of the subject to induce fluorescence emission from a fluorescence imaging agent 24 in the tissue of the subject (e.g., in blood), an image acquisition assembly 26 configured to acquire the time series of fluorescence images from the fluorescence emission, and a processor assembly 28 configured to utilize the acquired time series of fluorescence images (fluorescence signal intensity data) according to the various embodiments described herein.

In various embodiments, the light source 22 (FIG. 5) comprises, for example, an illumination module 30 (FIG. 6) comprising a fluorescence excitation source configured to generate an excitation light having a suitable intensity and a suitable wavelength for exciting the fluorescence imaging agent 24. The illumination module 30 in FIG. 6 comprises a laser diode 32 (e.g., which may comprise, for example, one or more fiber-coupled diode lasers) configured to provide an excitation light to excite the fluorescence imaging agent 24

(not shown). Examples of other sources of the excitation light which may be used in various embodiments include one or more LEDs, arc lamps, or other illuminant technologies of sufficient intensity and appropriate wavelength to excite the fluorescence imaging agent 24 in the tissue (e.g., in blood). For example, excitation of the fluorescence imaging agent 24 in blood, wherein the fluorescence imaging agent 24 is a fluorescence dye with near infra-red excitation and emission characteristics, may be performed using one or more 793 nm, conduction-cooled, single bar, fiber-coupled laser diode modules from DILAS Diode Laser Co, Germany.

Figure 5:
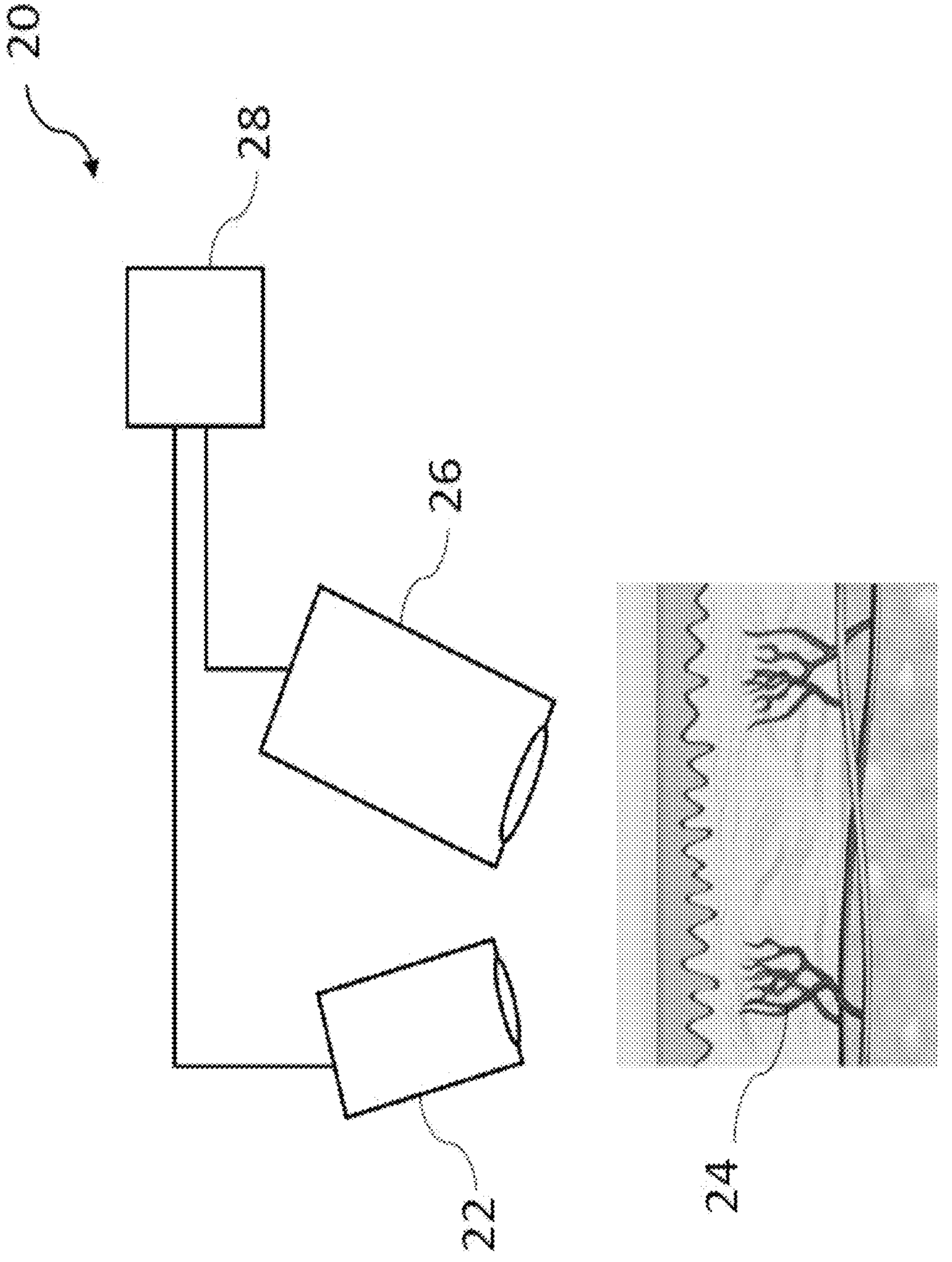
FIG. 5 illustrates an example fluorescence imaging system for use in acquiring data derived from fluorescence medical imaging according to some embodiments.

In various embodiments, the light output from the light source 22 in FIG. 5 may be projected through an optical element (e.g., one or more optical elements) to shape and guide the output being used to illuminate the tissue area of interest. The shaping optics may consist of one or more lenses, light guides, and/or diffractive elements so as to ensure a flat field over substantially the entire field of view of the image acquisition assembly 26. In particular embodiments, the fluorescence excitation source is selected to emit at a wavelength close to the absorption maximum of the fluorescence imaging agent 24 (e.g., ICG). For example, referring to the embodiment of the illumination module 30 in FIG. 6, the output 34 from the laser diode 32 is passed through one or more focusing lenses 36, and then through a homogenizing light pipe 38 such as, for example, light pipes commonly available from Newport Corporation, USA. Finally, the light is passed through an optical diffractive element 40 (e.g., one or more optical diffusers) such as, for example, ground glass diffractive elements also available from Newport Corporation, USA. Power to the laser diode 32 itself is provided by, for example, a high-current laser driver such as those available from Lumina Power Inc. USA. The laser may optionally be operated in a pulsed mode during the image acquisition process. In this embodiment, an optical sensor such as a solid state photodiode 42 is incorporated into the illumination module 30 and samples the illumination intensity produced by the illumination module 30 via scattered or diffuse reflections from the various optical elements. In various embodiments, additional illumination sources may be used to provide guidance when aligning and positioning the module over the area of interest.

Figure 7:
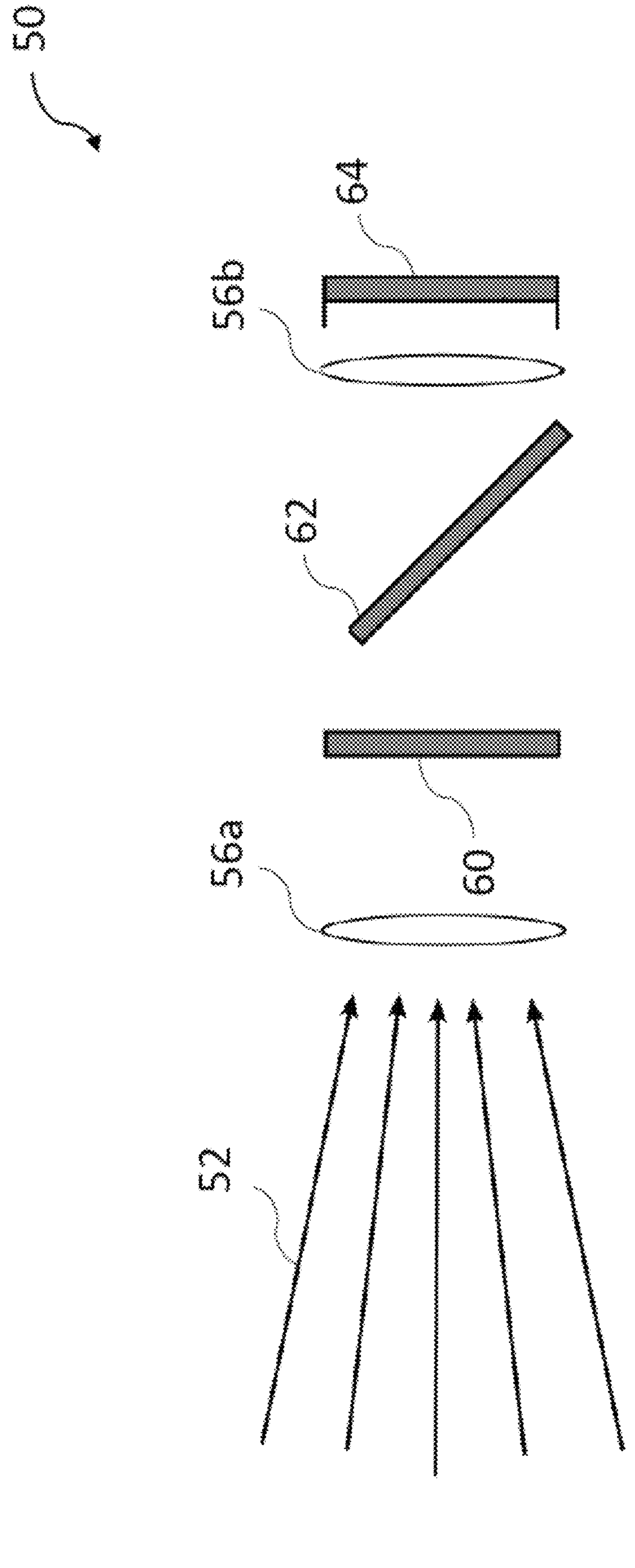
FIG. 7 illustrates an example camera module of the fluorescence imaging system according to some embodiments.

Referring back to FIG. 5, in various embodiments, the image acquisition assembly 26 may be a component of, for example, the fluorescence imaging system 20 configured to acquire the time series of fluorescence images (e.g., video) from the fluorescence emission from the fluorescence imaging agent 24. Referring to FIG. 7, there is shown an exemplary embodiment of an image acquisition assembly 26 comprising a camera module 50. As is shown in FIG. 7, the camera module 50 acquires images of the fluorescence emission 52 from the fluorescence imaging agent 24 in the tissue (e.g., in blood) (not shown) by using a system of imaging optics (e.g., front element **56*a*, rejection filter 56*b*, dichroic 60 and rear element 62) to collect and focus the fluorescence emission onto an image sensor assembly 64 comprising at least one 2D solid state image sensor. A rejection filter 56*b* may be, for example, a notch filter used to reject a band of wavelengths corresponding to the excitation light. A dichroic 60 may be, for example, a dichroic mirror used to selectively pass one subset of the incoming light wavelength spectrum and redirect remaining wavelengths off of the optical path for rejection or towards a separate image sensor. The solid state image sensor may be a charge coupled device (CCD), a CMOS sensor, a CID or similar 2D sensor technology. The charge that results from the optical signal transduced by the image sensor assembly 64 is converted to an electrical video signal, which includes both digital and analog video signals, by the appropriate read-out and amplification electronics in the camera module 50**.

According to some embodiments, excitation wavelength of about 800 nm+/−10 nm and emission wavelengths of >820 nm are used along with NIR compatible optics for ICG fluorescence imaging. A skilled person will appreciate that other excitation and emission wavelengths may be used for other imaging agents.

Referring back to FIG. 5, in various embodiments, the processor assembly 28 comprises, for example,

- a processor module (not shown) configured to perform various processing operations, including executing instructions stored on computer-readable medium, wherein the instructions cause one or more of the systems described herein to execute the methods and techniques described herein, and
- a data storage module (not shown) to record and store the data from the operations, as well as to store, in some embodiments, instructions executable by the processor module to implement the methods and techniques disclosed herein.

In various embodiments, the processor module comprises any computer or computing means such as, for example, a tablet, laptop, desktop, networked computer, or dedicated standalone microprocessor. Inputs are taken, for example, from the image sensor 64 of the camera module 50 shown in FIG. 7, from the solid state photodiode in the illumination module 30 in FIG. 6, and from any external control hardware such as a footswitch or remote-control. Output is provided to the laser diode driver, and optical alignment aids. In various embodiments, the processor assembly 28 (FIG. 5) may have a data storage module with the capability to save the time series of input data (e.g., image data) to a tangible non-transitory computer readable medium such as, for example, internal memory (e.g. a hard disk or flash memory), so as to enable recording and processing of data. In various embodiments, the processor module may have an internal clock to enable control of the various elements and ensure correct timing of illumination and sensor shutters. In various other embodiments, the processor module may also provide user input and graphical display of outputs. The fluorescence imaging system may optionally be configured with a video display (not shown) to display the images as they are being acquired or played back after recording, or further to visualize the data generated at various stages of the method as was described above.

Figure 6:
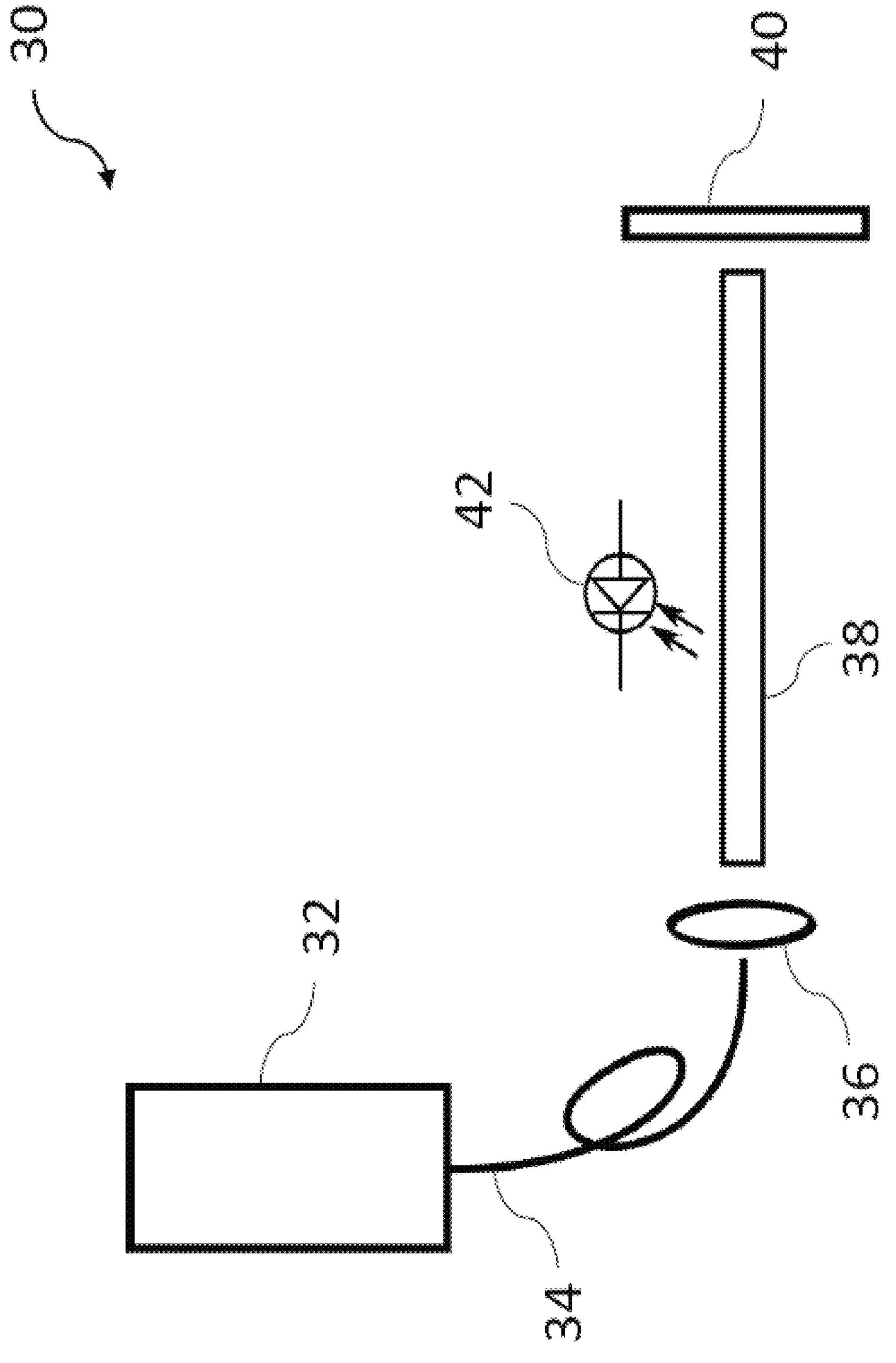
FIG. 6 illustrates an example illumination module of the fluorescence imaging system according to some embodiments.

In operation, and with continuing reference to the exemplary embodiments in FIGS. 5 to 7, as a result of the alignment of the subject according to the various embodiments, the subject is in a position for imaging where the anatomical area of interest of the subject is located beneath both the light source 22 and the image acquisition assembly 26 such that a substantially uniform field of illumination is produced across substantially the entire area of interest. In various embodiments, prior to the administration of the fluorescence imaging agent 24 to the subject, an image may be acquired of the area of interest for the purposes of background deduction. For example, in order to do this, the operator of the fluorescence imaging system 20 in FIG. 5 may initiate the acquisition of the time series of fluorescence images (e.g., video) by depressing a remote switch or foot-control, or via a keyboard (not shown) connected to the processor assembly 28. As a result, the light source 22 is turned on and the processor assembly 28 begins recording the fluorescence image data provided by the image acquisition assembly 26. In lieu of the pulsed mode discussed above, it will be understood that, in some embodiments, the light source 22 can comprise an emission source which is continuously on during the image acquisition sequence. When operating in the pulsed mode of the embodiment, the image sensor 64 in the camera module 50 (FIG. 7) is synchronized to collect fluorescence emission following the laser pulse produced by the diode laser 32 in the illumination module 30 (FIG. 6). In this way, maximum fluorescence emission intensity is recorded, and signal-to-noise ratio is optimized. In this embodiment, the fluorescence imaging agent 24 is administered to the subject and delivered to the area of interest via arterial flow. Acquisition of the time series of fluorescence images is initiated, for example, shortly after administration of the fluorescence imaging agent 24, and the time series of fluorescence images from substantially the entire area of interest are acquired throughout the ingress of the fluorescence imaging agent 24. The fluorescence emission from the region of interest is collected by the collection optics of the camera module 50. Residual ambient and reflected excitation light is attenuated by subsequent optical elements (e.g., optical element 60 in FIG. 7 which may be a filter) in the camera module 50 so that the fluorescence emission can be acquired by the image sensor assembly 64 with minimal interference by light from other sources.

In various embodiments, the processor is in communication with the imaging system or is a component of the imaging system. The program code or other computer-readable instructions, according to the various embodiments, can be written and/or stored in any appropriate programming language and delivered to the processor in various forms, including, for example, but not limited to information permanently stored on non-writeable storage media (e.g., read-only memory devices such as ROMs or CD-ROM disks), information alterably stored on writeable storage media (e.g., hard drives), information conveyed to the processor via transitory mediums (e.g., signals), information conveyed to the processor through communication media, such as a local area network, a public network such as the Internet, or any type of media suitable for storing electronic instruction. In various embodiments, the tangible non-transitory computer readable medium comprises all computer-readable media. In some embodiments, computer-readable instructions for performing one or more of the methods or techniques discussed herein may be stored solely on non-transitory computer readable media.

In some embodiments, the system and method for alignment of the subject for medical imaging may be a component of a medical imaging system such as the fluorescence medical imaging system 20, which acquires the medical image data and is further configured to align the subject for such imaging. In embodiments where the alignment system is a component of the imaging system, such as the fluorescence imaging system described above, the light source, the image acquisition assembly and the processor of the imaging system may function as the camera assembly and the processor of the alignment system. A skilled person will appreciate that imaging systems other than fluorescence imaging systems may be employed for use with alignment systems such as those described herein, depending on the type of imaging being performed.

Example Imaging Agents for Use in Generating Image Data

According to some embodiments, in fluorescence medical imaging applications, the imaging agent is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 μM to about 10 μM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 μM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some embodiments, the fluorescence imaging agent used in combination with the methods and systems described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

Examples of Image Data Alignment According to an Embodiment

FIG. 2 illustrates example results generated according to the various embodiments described above relating to an application of the methods and systems to alignment of a subject for fluorescence imaging. The fluorescence image data was generated using a fluorescence imaging system (available from NOVADAQ® Technologies Inc.), and ICG was used as the fluorescence imaging agent.

FIG. 2 illustrates image data alignment according to an embodiment where the alignment reference image (indicated by the solid white arrow) is simultaneously displayed to the user on a display with video image data (indicated by the pattern arrow) during a subsequent assessment of the subject following the initial assessment during which the alignment reference image was generated. The initial, or preceding, assessment may be from a previous patient visit or interaction (e.g., if assessing the course of wound and/or tissue healing over multiple visits), or from an earlier point in time during the same visit (e.g., if taking multiple intra-operative image assessments during a surgical procedure). The dashed line shows the degree of misalignment or offset of the video image data with the alignment reference image. Without correcting for such misalignment, the fluorescence image data acquired during the subsequent assessment would not be suitable for an accurate comparison, including a quantitative assessment, with the image data from the initial assessment, and any clinical conclusions drawn from such data would therefore not be accurate. A user, seeing such misalignment (and/or a system detecting such misalignment), based on a comparison of the video image data and the simultaneously displayed alignment reference image, may align the video image data to mimic the image acquisition conditions from the preceding assessment, as was described in the various embodiments, without having to rely solely on his or her experience, judgment, memory, and estimation as to the proper alignment. Instead, the user may be provided with dynamic visual feedback, including the ability to view both the video image data and the alignment reference image at once, and the user further may be provided with user-interface cues provided by the system including indications of an offset distance, indication of a metric indicating the strength of the current alignment, boundaries or markers to aid achieving alignment, and or express indications (e.g., visual, auditory, or haptic notifications) that sufficient alignment has or has not been achieved. By leveraging these forms of dynamic visual (and/or auditory and/or haptic) feedback, a system may achieve accurate alignment more reliably and more efficiently. Following such alignment, fluorescence imaging can be initiated as was described above in connection with the various embodiments. Proper alignment for medical imaging is important as it aids qualitative and quantitative monitoring of clinical outcomes over time in a controlled manner.

Thus, the methods and systems in accordance with the various embodiments are intuitive and user friendly and may be used by inexperienced and/or experienced users to minimize inaccuracies in medical imaging and analysis, such as for example fluorescence imaging for the analysis of blood flow dynamics, including tissue perfusion analysis. Tissue perfusion relates to the microcirculatory flow of blood per unit tissue volume in which oxygen and nutrients are provided to and waste is removed from the capillary bed of the tissue being perfused. A distinction should be drawn between vascular blood flow and tissue blood perfusion, namely that tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

The invention claimed is:

1. A method of aligning a camera, the method comprising:
- receiving a reference image of an anatomical region of a subject, the anatomical region comprising a target tissue;
- processing the reference image to generate an alignment reference image;
- displaying the alignment reference image on a display concurrently with real-time video of the anatomical region acquired from the camera;
- dynamically updating the displayed real-time video to reflect adjustments to a current alignment of the camera relative to the anatomical region of the subject; and
- displaying the real-time video and the alignment reference image as overlaid with one another when the current alignment of the camera is aligned with a predefined alignment associated with the reference image;
- determining that the current alignment is aligned with the predefined alignment, wherein the determination is performed before initiating illuminating, by a light source, of the target tissue to induce fluorescence emission and is performed before initiating capturing, by the camera, of a time series of fluorescence input data from the fluorescence emission;
- in response to the determining that the current alignment is aligned with the predefined alignment:
  - initiating the illuminating, by the light source, the target tissue to induce the fluorescence emission;
  - initiating the capturing, by the camera, the time series of fluorescence input data from the fluorescence emission, wherein the camera is configured to receive fluorescence images for fluorescence medical imaging.

2. The method of claim 1, wherein the fluorescence medical imaging comprises quantitative fluorescence imaging, qualitative fluorescence imaging, or a combination thereof.

3. The method of claim 1, comprising, in response to detecting that the current alignment is not aligned with the predefined alignment, ceasing the illuminating and the capturing.

4. The method of claim 1, wherein inducing fluorescence emission comprises inducing fluorescence emission from an endogenous fluorophore, from an exogenous fluorescence imaging agent, or a combination thereof.

5. The method of claim 4, wherein the exogenous fluorescence imaging agent comprises indocyanine green (ICG).

6. The method of claim 1, further comprising quantifying the fluorescence input data.

7. The method of claim 1, further comprising, while the current alignment is aligned with the predefined alignment, acquiring the real-time video and processing the real-time video to quantify the target tissue.

8. The method of claim 7, wherein the acquiring and processing of the real time video is initiated in response to detecting that the current alignment is aligned with the predefined alignment.

9. The method of claim 7, wherein quantifying the target tissue comprises calculating a dimension of the target tissue.

10. The method of claim 7, further comprising, in response to detecting that the current alignment is not aligned with the predefined alignment, ceasing the acquiring and processing of the real-time video.

11. The method of claim 1, wherein receiving the reference image comprises receiving the reference image from a camera.

12. The method of claim 1, wherein receiving the reference image comprises retrieving stored data representing the reference image.

13. The method of claim 1, wherein the reference image is a white light image, a white light-derived image, a fluorescence image, a fluorescence-derived image, or a combination of any one or more thereof.

14. The method of claim 1, wherein processing the reference image to generate the alignment reference image comprises applying transparency to the reference image.

15. The method of claim 1, further comprising displaying an alignment indicator on the display, wherein the alignment indicator indicates a difference between the current alignment and the predefined alignment, and wherein the alignment indicator is distinct from the real-time video and the alignment reference image.

16. The method of claim 15, wherein indicating a difference between the current alignment and the predefined alignment comprises displaying a line between a first portion of the alignment reference image depicting a portion of the anatomical region and a corresponding portion of the real-time video depicting the portion of the anatomical region.

17. The method of claim 16, wherein the line indicates a direction in which the current alignment should be adjusted to align with the predefined alignment.

18. The method of claim 1, further comprising, in response to detecting that the current alignment is aligned with the predefined alignment, displaying on the display a notification that the current alignment is aligned with the predefined alignment, wherein the notification is distinct from the real-time video and the alignment reference image.

19. The method of claim 1, further comprising, in response to detecting that the current alignment is aligned with the predefined alignment, providing one of an auditory and a haptic notification that the current alignment is aligned with the predefined alignment.

20. The method of claim 1, wherein the reference image comprises one or both of a white light image and a processed image.

21. The method of claim 1, wherein the real-time video comprises one or both of a white light image and a processed image.

22. The method of claim 1, further comprising applying an algorithm to determine that the current alignment is aligned with the predefined alignment.

23. The method of claim 22, wherein applying the algorithm comprises calculating an image transformation matrix including a translation and a rotation for aligning the current alignment and the predefined alignment.

24. A fluorescence imaging agent for use in the method of claim 1 for aligning the camera.

25. The fluorescence imaging agent of claim 24, wherein aligning the camera comprises aligning for blood flow imaging, tissue perfusion imaging, lymphatic imaging, or a combination thereof.

26. The fluorescence imaging agent of claim 25, wherein the blood flow imaging, tissue perfusion imaging, and/or lymphatic imaging comprises blood flow imaging, tissue perfusion imaging, and/or lymphatic imaging during an invasive surgical procedure, a minimally invasive surgical procedure, or during a non-invasive surgical procedure.

27. The fluorescence imaging agent of claim 26, wherein the invasive surgical procedure comprises a cardiac-related surgical procedure or a reconstructive surgical procedure.

28. The fluorescence imaging agent of claim 27, wherein the cardiac-related surgical procedure comprises a cardiac coronary artery bypass graft (CABG) procedure.

29. The fluorescence imaging agent of claim 28, wherein the CABG procedure is on pump or off pump.

30. The method of claim 1, wherein the camera is mounted on a camera arm.

31. An alignment system comprising:
- a display;
- a camera;
- a processor; and
- memory storing instructions that, when executed by the processor, cause the processor to:
  - receive a reference image of an anatomical region of a subject, the anatomical region comprising a target tissue;
  - process the reference image to generate an alignment reference image;
  - display the alignment reference image on a display concurrently with real-time video of the anatomical region acquired from the camera;
  - update the displayed real-time video to reflect adjustments to a current alignment of the camera relative to the anatomical region of the subject; and
  - display the real-time video and the alignment reference image as overlaid with one another when the current alignment of the camera is aligned with a predefined alignment associated with the reference image;
  - determine that the current alignment is aligned with the predefined alignment, wherein the determination is performed before initiating illuminating, by a light source, of the target tissue to induce fluorescence emission and is performed before initiating capturing, by the camera, of a time series of fluorescence input data from the fluorescence emission;
- in response to the determining that the current alignment is aligned with the predefined alignment, the instructions further cause the processor to:
  - initiate the illumination, by the light source, of the target tissue to induce the fluorescence emission;
  - initiate the capture, by the camera, of the time series of fluorescence input data from the fluorescence emission, wherein the camera is configured to receive fluorescence images for fluorescence medical imaging.

32. The system of claim 31, wherein the fluorescence images are for fluorescence imaging, the fluorescence imaging comprising quantitative fluorescence imaging, qualitative fluorescence imaging, or a combination thereof.

33. The system of claim 31, wherein the instructions cause the processor to, in response to detecting that the current alignment is not aligned with the predefined alignment, cease the illuminating and the capturing.

34. The system of claim 31, wherein inducing fluorescence emission comprises inducing fluorescence emission from an endogenous fluorophore, from an exogenous fluorescence imaging agent, or a combination thereof.

35. The system of claim 34, wherein the exogenous fluorescence imaging agent comprises indocyanine green (ICG).

36. The system of claim 35, wherein the instructions cause the processor to quantify the fluorescence input data.

37. The system of claim 31, wherein the instructions cause the processor to, while the current alignment is aligned with the predefined alignment, acquire the real-time video and process the real-time video to quantify the target tissue.

38. The system of claim 37, wherein the acquiring and processing of the real time video is initiated in response to detecting that the current alignment is aligned with the predefined alignment.

39. The system of claim 37, wherein quantifying the target tissue comprises calculating a dimension of the target tissue.

40. The system of claim 37, wherein the instructions cause the processor to, in response to detecting that the current alignment is not aligned with the predefined alignment, cease the acquiring and processing of the real-time video.

41. The system of claim 31, wherein receiving the reference image comprises receiving the reference image from a camera.

42. The system of claim 31, wherein receiving the reference image comprises retrieving stored data representing the reference image.

43. The system of claim 31, wherein the reference image is a white light image, a white light-derived image, a fluorescence image, a fluorescence-derived image, or a combination of any one or more thereof.

44. The system of claim 31, wherein processing the reference image to generate the alignment reference image comprises applying transparency to the reference image.

45. The system of claim 31, wherein the instructions cause the processor to display an alignment indicator on the display, wherein the alignment indicator indicates a difference between the current alignment and the predefined alignment, and wherein the alignment indicator is distinct from the real-time video and the alignment reference image.

46. The system of claim 45, wherein indicating a difference between the current alignment and the predefined alignment comprises displaying a line between a first portion of the alignment reference image depicting a portion of the anatomical region and a corresponding portion of the real-time video depicting the portion of the anatomical region.

47. The system of claim 46, wherein the line indicates a direction in which the current alignment should be adjusted to align with the predefined alignment.

48. The system of claim 47, wherein the instructions cause the processor to, in response to detecting that the current alignment is aligned with the predefined alignment, display on the display a notification that the current alignment is aligned with the predefined alignment, wherein the notification is distinct from the real-time video and the alignment reference image.

49. The system of claim 31, wherein the instructions cause the processor to, in response to detecting that the current alignment is aligned with the predefined alignment, provide one of an auditory and a haptic notification that the current alignment is aligned with the predefined alignment.

50. The system of claim 31, wherein the reference image comprises one or both of a white light image and a processed image.

51. The system of claim 31, wherein the real-time video comprises one or both of a white light image and a processed image.

52. The system of claim 31, wherein the instructions cause the processor to apply an algorithm to determine that the current alignment is aligned with the predefined alignment.

53. The system of claim 52, wherein applying the algorithm comprises calculating an image transformation matrix including a translation and a rotation for aligning the current alignment and the predefined alignment.

54. A kit for aligning a camera, the kit comprising the system of claim 31 and a fluorescence imaging agent.

55. A fluorescence imaging agent for use in the system of claim 31 for aligning the camera.

56. The system of claim 31, comprising a camera arm on which the camera is mounted.

57. A non-transitory computer readable storage medium storing instructions, wherein the instructions are executable by a system having a display, a camera, and a processor to cause the system to:

receive a reference image of an anatomical region of a subject, the anatomical region comprising a target tissue;

process the reference image to generate an alignment reference image;

display the alignment reference image on a display concurrently with real-time video of the anatomical region acquired from the camera;

update the displayed real-time video to reflect adjustments to a current alignment of the camera relative to the anatomical region of the subject; and display the real-time video and the alignment reference image as overlaid with one another when the current alignment of the camera is aligned with a predefined alignment associated with the reference image;

determine that the current alignment is aligned with the predefined alignment, wherein the determination is performed before initiating illuminating, by a light source, of the target tissue to induce fluorescence emission and is performed before initiating capturing, by the camera, of a time series of fluorescence input data from the fluorescence emission;

in response to the determining that the current alignment is aligned with the predefined alignment, the instructions further cause the processor to:

initiate the illumination, by the light source, of the target tissue to induce the fluorescence emission;

initiate the capture, by the camera, of the time series of fluorescence input data from the fluorescence emission, wherein the camera is configured to receive fluorescence images for fluorescence medical imaging.

58. The non-transitory computer readable storage medium of claim 57, wherein the fluorescence images are for fluorescence imaging, the fluorescence imaging comprising quantitative fluorescence imaging, qualitative fluorescence imaging, or a combination thereof.

59. The non-transitory computer readable storage medium of claim 57, wherein the instructions cause the processor to, in response to detecting that the current alignment is not aligned with the predefined alignment, cease the illuminating and the capturing.

60. The non-transitory computer readable storage medium of claim 57, wherein inducing fluorescence emission comprises inducing fluorescence emission from an endogenous fluorophore, from an exogenous fluorescence imaging agent, or a combination thereof.

61. The non-transitory computer readable storage medium of claim 60, wherein the exogenous fluorescence imaging agent comprises indocyanine green (ICG).

62. The non-transitory computer readable storage medium of claim 61, wherein the instructions cause the processor to quantify the fluorescence input data.

63. The non-transitory computer readable storage medium of claim 57, wherein the instructions cause the processor to, while the current alignment is aligned with the predefined alignment, acquire the real-time video and process the real-time video to quantify the target tissue.

64. The non-transitory computer readable storage medium of claim 63, wherein the acquiring and processing of the real time video is initiated in response to detecting that the current alignment is aligned with the predefined alignment.

65. The non-transitory computer readable storage medium of claim 63, wherein quantifying the target tissue comprises calculating a dimension of the target tissue.

66. The non-transitory computer readable storage medium of claim 63, wherein the instructions cause the processor to, in response to detecting that the current alignment is not aligned with the predefined alignment, cease the acquiring and processing of the real-time video.

67. The non-transitory computer readable storage medium of claim 57, wherein receiving the reference image comprises receiving the reference image from a camera.

68. The non-transitory computer readable storage medium of claim 57, wherein receiving the reference image comprises retrieving stored data representing the reference image.

69. The non-transitory computer readable storage medium of claim 57, wherein the reference image is a white light image, a white light-derived image, a fluorescence image, a fluorescence-derived image, or a combination of any one or more thereof.

70. The non-transitory computer readable storage medium of claim 57, wherein processing the reference image to generate the alignment reference image comprises applying transparency to the reference image.

71. The non-transitory computer readable storage medium of claim 57, wherein the instructions cause the processor to display an alignment indicator on the display, wherein the alignment indicator indicates a difference between the current alignment and the predefined alignment, and wherein the alignment indicator is distinct from the real-time video and the alignment reference image.

72. The non-transitory computer readable storage medium of claim 71, wherein indicating a difference between the current alignment and the predefined alignment comprises displaying a line between a first portion of the alignment reference image depicting a portion of the anatomical region and a corresponding portion of the real-time video depicting the portion of the anatomical region.

73. The non-transitory computer readable storage medium of claim 72, wherein the line indicates a direction in which the current alignment should be adjusted to align with the predefined alignment.

74. The non-transitory computer readable storage medium of claim 73, wherein the instructions cause the processor to, in response to detecting that the current alignment is aligned with the predefined alignment, display on the display a notification that the current alignment is aligned with the predefined alignment, wherein the notification is distinct from the real-time video and the alignment reference image.

75. The non-transitory computer readable storage medium of claim 57, wherein the instructions cause the processor to, in response to detecting that the current alignment is aligned with the predefined alignment, provide one of an auditory and a haptic notification that the current alignment is aligned with the predefined alignment.

76. The non-transitory computer readable storage medium of claim 57, wherein the reference image comprises one or both of a white light image and a processed image.

77. The non-transitory computer readable storage medium of claim 57, wherein the real-time video comprises one or both of a white light image and a processed image.

78. The non-transitory computer readable storage medium of claim 57, wherein the instructions cause the processor to apply an algorithm to determine that the current alignment is aligned with the predefined alignment.

79. The non-transitory computer readable storage medium of claim 78, wherein applying the algorithm comprises calculating an image transformation matrix including a translation and a rotation for aligning the current alignment and the predefined alignment.

80. The non-transitory computer readable storage medium of claim 57, wherein the camera is mounted on a camera arm.

* * * * *